United States Patent
Roth

(10) Patent No.: US 7,505,131 B2
(45) Date of Patent: Mar. 17, 2009

(54) METHODS AND SYSTEMS FOR DYNAMIC RANGE EXPANSION

(75) Inventor: Wayne D. Roth, Leander, TX (US)

(73) Assignee: Luminex Corporation, Austin, TX (US)

( * ) Notice: Subject to any disclaimer, the term of this patent is extended or adjusted under 35 U.S.C. 154(b) by 0 days.

(21) Appl. No.: 12/043,312

(22) Filed: Mar. 6, 2008

(65) Prior Publication Data

US 2008/0151240 A1 Jun. 26, 2008

Related U.S. Application Data

(62) Division of application No. 11/036,571, filed on Jan. 13, 2005, now Pat. No. 7,362,432.

(60) Provisional application No. 60/536,465, filed on Jan. 14, 2004.

(51) Int. Cl.
*G01J 3/30* (2006.01)
*G01J 3/40* (2006.01)

(52) U.S. Cl. ........................ 356/317; 356/303

(58) Field of Classification Search ............. 356/302, 356/303, 305, 307, 317, 318, 319, 326, 330; 250/458.1
See application file for complete search history.

(56) References Cited

U.S. PATENT DOCUMENTS

| | | | |
|---|---|---|---|
| 4,193,691 A * | 3/1980 | Fjarlie | 356/330 |
| 5,367,474 A * | 11/1994 | Auer et al. | 702/21 |
| 5,736,330 A | 4/1998 | Fulton | |
| 5,818,583 A | 10/1998 | Sevick-Muraca et al. | |
| 5,981,180 A | 11/1999 | Chandler et al. | |
| 6,057,107 A | 5/2000 | Fulton | |
| 6,268,222 B1 | 7/2001 | Chandler et al. | |
| 6,355,921 B1 | 3/2002 | Staton et al. | |
| 6,449,562 B1 * | 9/2002 | Chandler et al. | 702/19 |
| 6,514,295 B1 | 2/2003 | Chandler et al. | |
| 6,524,793 B1 | 2/2003 | Chandler et al. | |
| 6,528,165 B2 | 3/2003 | Chandler | |
| 6,592,822 B1 * | 7/2003 | Chandler | 422/82.05 |
| 6,649,414 B1 | 11/2003 | Chandler et al. | |
| 6,825,929 B2 | 11/2004 | Dorsel | |
| 6,859,275 B2 * | 2/2005 | Fateley et al. | 356/330 |
| 7,054,003 B2 | 5/2006 | Dorsel | |
| 7,304,310 B1 * | 12/2007 | Shortt et al. | 250/372 |
| 7,318,336 B2 * | 1/2008 | Roth et al. | 73/1.02 |
| 2003/0087282 A1 | 5/2003 | Oshida et al. | |
| 2003/0096302 A1 | 5/2003 | Yguerabide et al. | |
| 2003/0218746 A1 | 11/2003 | Sampas | |
| 2008/0087068 A1 * | 4/2008 | Roth et al. | 73/1.34 |

* cited by examiner

OTHER PUBLICATIONS

International Search Report, PCT/US2005/001866, mailed Jun. 28, 2005.

*Primary Examiner*—Michael A Lyons
*Assistant Examiner*—Scott M Richey
(74) *Attorney, Agent, or Firm*—Mollie E. Lettang; Charles D. Huston; Daffer McDaniel, LLP

(57) ABSTRACT

Methods and systems for expanding the dynamic range of a system are provided. One method includes splitting fluorescent light emitted by a particle into multiple light paths having different intensities, detecting the fluorescent light in the multiple light paths with different channels to generate multiple signals, and determining which of the channels is operating in a linear range based on the multiple signals. The method also includes altering the signal generated by the channel operating in the linear range to compensate for the different intensities. Another method includes illuminating a particle in multiple illumination zones with light having different intensities and separately detecting fluorescent light emitted by the particle while located in the multiple illumination zones to generate multiple signals. The method also includes determining which of the signals is located in a linear range and altering the signal located in the linear range to compensate for the different intensities.

14 Claims, 3 Drawing Sheets

METHODS AND SYSTEMS FOR DYNAMIC RANGE EXPANSION

PRIORITY CLAIM

This application is a divisional application from prior U.S. patent application Ser. No. 11/036,571 filed Jan. 13, 2005 which claims priority to U.S. Provisional Application No. 60/536,465 filed Jan. 14, 2004, which are incorporated by reference as if fully set forth herein.

BACKGROUND OF THE INVENTION

1. Field of the Invention

This invention generally relates to methods and systems for dynamic range expansion. Certain embodiments relate to methods and systems for dynamic range expansion in flow cytometry applications.

2. Description of the Related Art

The following descriptions and examples are not admitted to be prior art by virtue of their inclusion within this section.

Generally, flow cytometers can be used to provide measurements of the intensity of fluorescent light emitted by polystyrene beads, human cells, or other discrete substances due to exposure to an excitation source such as a laser as they pass linearly through a flow chamber. In some systems, there are four measurements that are performed: the level of light scattered by a particle at 90° to the excitation source, two or more measurements of fluorescence used to determine the particle "identity," and an additional fluorescence measurement typically used to determine and/or quantify a surface chemical reaction of interest. Each of the fluorescent measurements is typically made at a different wavelength.

The fluorescence measurement of the surface chemical reaction is typically quantified by optically projecting an image of the particle as it passes through an illumination zone of the excitation source on the photosensitive area of a photomultiplier tube (PMT) or another photosensitive detector. The output of the detector is a current pulse, which is then conditioned by analog electronics and digitized by an analog to digital (A/D) converter. The resultant digital values obtained from the A/D converter may be further conditioned in the digital domain by a digital signal processing (DSP) algorithm. The end product per particle is a single integer value, which is proportional to the chemical reaction on the surface of the particle. The fluorescent measurement(s) related to the particle identity may be performed in a similar manner. Alternatively, the integer values of the fluorescence emitted by a particle corresponding to the particle identity may be used in a different manner to determine the particle identity (e.g., by a ratio of the integer values, etc.).

The dynamic range (DR) of a flow cytometry system as described above may be generally defined as the ratio of the measurable maximum fluorescence level to measurable minimum fluorescence level. In this manner, the higher the DR, the more useful the system is at discriminating the level of chemical reaction and/or the particle identity.

The DR of currently available flow cytometers is limited by the DR of each individual element in the system (e.g., the major components including the photosensitive detector, analog electronics, and A/D converter). Typically, the photonic nature of light and noise inherent to the detector's amplification method define the detection limit at the low end of the scale, and the analog electronics and A/D converter constrain the maximum measurable fluorescence level. With commonly available off-the-shelf linear components, the useful dynamic range of flow cytometers is limited to approximately 4 decades (1 to 10,000). Usually a flow cytometry system is designed and calibrated to discern the smallest possible fluorescent signal level from the particles thereby sacrificing the ability to measure the very brightest levels of fluorescence due to the DR limits of the system.

In U.S. Pat. No. 5,367,474 to Auer et al., which is incorporated by reference as if fully set forth herein, a method to increase the DR of a flow cytometer is shown, which uses an electrical gain stage inserted between the first electrical amplifier and subsequent processing circuitry. A bypass path around the amplifier is also provided. For small signal inputs, the additional amplifier stage is used to increase the small signal, while the bypass path can be selected for signals that are already large.

This technique, while seemingly adequate to cover both small and large signal ranges, is disadvantageous in that the electrical gain stage, when inserted in the signal path, adds noise to the small signal level. It is known to those skilled in the art of flow cytometer design that the best signal-to-noise ratio occurs when the maximum electrical system gain occurs in the first circuitry stages. Thus, the bias on the photomultiplier tube, which determines its photon to electron gain factor, and is the actual first gain stage, should be maximized, and subsequent gain stages minimized.

Accordingly, it would be desirable to increase the dynamic range of a measurement system such as a flow cytometer in the first gain stage to produce the maximum signal-to-noise ratio without adding noise to small signal levels.

SUMMARY OF THE INVENTION

The following description of various embodiments of methods and systems for dynamic range expansion is not to be construed in any way as limiting the subject matter of the appended claims.

One embodiment relates to a method for expanding a dynamic range of a system that includes splitting fluorescent light emitted by a particle into multiple light paths. The fluorescent light in the multiple light paths has different intensities. The method also includes detecting the fluorescent light in the multiple light paths with different channels to generate multiple signals. Each of the multiple signals represents the fluorescent light in one of the multiple light paths. In addition, the method includes determining which of the different channels is operating in a linear range based on the multiple signals. The method further includes altering the signal generated by the channel determined to be operating in the linear range to compensate for the different intensities.

In one embodiment, the fluorescent light emitted by the particle corresponds to an identity of the particle. In a different embodiment, the fluorescent light emitted by the particle corresponds to a molecule reacted with an additional molecule attached to the particle. In some embodiments, the system may be configured as a flow cytometer. In another embodiment, the method includes determining an intensity of the fluorescent light emitted by the particle from the altered signal. In an additional embodiment, altering the signal increases the dynamic range for the system.

In a further embodiment, the fluorescent light in a first of the multiple light paths is lower in intensity than the fluorescent light in a second of the multiple light paths. In such an embodiment, the method may include prior to the detecting step, decreasing the intensity of the fluorescent light in the first of the multiple light paths. Each of the embodiments of the method described above may include any other step(s) described herein.

Another embodiment relates to a system configured to have an expanded dynamic range. The system includes an optical component configured to split fluorescent light emitted by a particle into multiple light paths. The fluorescent light in the multiple light paths has different intensities. The system also includes different channels configured to separately detect the fluorescent light in the multiple light paths and to generate multiple signals. Each of the multiple signals represents the fluorescent light in one of the multiple light paths. In addition, the system includes a processor configured to determine which of the different channels is operating in a linear range based on the multiple signals and to alter the signal generated by the channel determined to be operating in the linear range to compensate for the different intensities.

The fluorescent light emitted by the particle may correspond to an identity of the particle. Alternatively, the fluorescent light emitted by the particle may correspond to a molecule reacted with an additional molecule attached to the particle. In some embodiments, the system may be configured as a flow cytometer. In an additional embodiment, the processor may be configured to determine an intensity of the fluorescent light emitted by the particle from the altered signal. Altering of the signal preferably increases the dynamic range of the system.

In one embodiment, each of the different channels includes a photomultiplier tube, a photodiode, an avalanche photodiode, a charge coupled device (CCD), or a complementary metal-oxide-semiconductor (CMOS) detector. In an additional embodiment, each of the different channels includes any type of diode detector known in the art or any type of linear array type detector. In another embodiment, the fluorescent light in a first of the multiple light paths is lower in intensity than the fluorescent light in a second of the multiple light paths. In one such embodiment, the system includes an additional optical component positioned in the first of the multiple light paths between the optical component and one of the different channels. The additional optical component may be configured to decrease the intensity of the fluorescent light in the first of the multiple light paths. Each of the embodiments of the system described above may be further configured as described herein.

An additional embodiment relates to a different method for expanding a dynamic range of a system. This method includes illuminating a particle in multiple illumination zones with light having different intensities. The method also includes separately detecting fluorescent light emitted by the particle while the particle is located in the multiple illumination zones to generate multiple signals. Each of the multiple signals is representative of the fluorescent light emitted by the particle while located in one of the multiple illumination zones. In addition, the method includes determining which of the multiple signals is located in a linear range. The method further includes altering the signal located in the linear range to compensate for the different intensities.

In one embodiment, the multiple illumination zones are spaced apart along a flow path of the particle. A first of the multiple illumination zones in which the particle is first located is lower in intensity than a second of the multiple illumination zones in which the particle is subsequently located. In some embodiments, the fluorescent light emitted by the particle corresponds to an identity of the particle. In other embodiments, the fluorescent light emitted by the particle corresponds to a molecule reacted with an additional molecule attached to the particle. Each of the embodiments of the method described above may include any other step(s) described herein.

A further embodiment relates to a different system configured to have an expanded dynamic range. The system includes an illumination subsystem configured to illuminate a particle in multiple illumination zones with light having different intensities. The system also includes a detection subsystem configured to separately detect fluorescent light emitted by the particle while the particle is located in the multiple illumination zones and to generate multiple signals. Each of the multiple signals represents the fluorescent light emitted by the particle while the particle is located in one of the multiple illumination zones. In addition, the system includes a processor configured to determine which of the multiple signals is located in a linear range and to alter the signal located in the linear range to compensate for the different intensities.

In one embodiment, the multiple illumination zones are spaced apart along a flow path of the particle. A first of the multiple illumination zones in which the particle is first located is lower in intensity than a second of the multiple illumination zones in which the particle is subsequently located.

In some embodiments, the illumination subsystem includes a single light source. In one such embodiment, the illumination subsystem also includes a glass slide arranged in a path of a light beam emitted by the single light source and further arranged at an angle with respect to the light beam. In a different embodiment, the illumination subsystem includes a wedge of glass with non-parallel surfaces arranged in a path of a light beam emitted by the single light source. In other embodiments, the illumination subsystem includes multiple fiber optic cables coupled to the single light source. In yet another embodiment, the illumination subsystem includes one or more demultiplexers coupled to the single light source. In still another embodiment, the illumination subsystem includes a diffraction grating arranged in a path of a light beam emitted by the single light source. In another embodiment, the illumination subsystem may include two or more light sources.

In some embodiments, the detection subsystem includes a single detector. The single detector may include a photomultiplier tube or any other suitable detector known in the art such as a photodiode, an avalanche photodiode, a CCD, a CMOS detector, or any other suitable type of diode or linear array detector known in the art. In a different embodiment, the detection subsystem includes multiple detectors. Each of the multiple detectors may include a photomultiplier tube or any other suitable detector known in the art such as a photodiode, an avalanche photodiode, a CCD, a CMOS detector, or any other suitable type of diode or linear array detector known in the art. Each of the embodiments of the system described above may be further configured as described herein.

BRIEF DESCRIPTION OF THE DRAWINGS

Other objects and advantages of the invention will become apparent upon reading the following detailed description and upon reference to the accompanying drawings in which.

Figure 1:
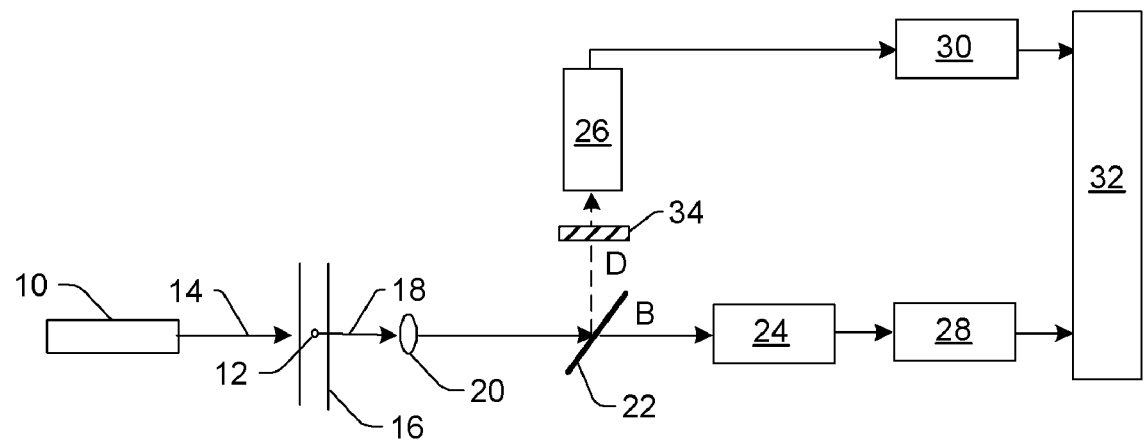
FIG. 1 is a schematic diagram illustrating a cross-sectional view of one embodiment of a system configured to have an expanded dynamic range (DR) that includes an optical component configured to split fluorescent light into multiple light paths and different channels configured to separately detect the fluorescent light in the multiple light paths.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Although embodiments are described herein with respect to particles, it is to be understood that the systems and methods described herein may also be used with microspheres, polystyrene beads, microparticles, gold nanoparticles, quantum dots, nanodots, nanoparticles, nanoshells, beads, microbeads, latex particles, latex beads, fluorescent beads, fluorescent particles, colored particles, colored beads, tissue, cells, micro-organisms, organic matter, non-organic matter, or any other discrete substances known in the art. The particles may serve as vehicles for molecular reactions. Examples of appropriate particles are illustrated in U.S. Pat. No. 5,736,330 to Fulton, U.S. Pat. No. 5,981,180 to Chandler et al., U.S. Pat. No. 6,057,107 to Fulton, U.S. Pat. No. 6,268,222 to Chandler et al., U.S. Pat. No. 6,449,562 to Chandler et al., U.S. Pat. No. 6,514,295 to Chandler et al., U.S. Pat. No. 6,524,793 to Chandler et al., and U.S. Pat. No. 6,528,165 to Chandler, which are incorporated by reference as if fully set forth herein. The systems and methods described herein may be used with any of the particles described in these patents. In addition, particles for use in flow cytometry may be obtained from manufacturers such as Luminex Corp., Austin, Tex. The terms "particles" and "microspheres" are used interchangeably herein.

In addition, the types of particles that are compatible with the systems and methods described herein include particles with fluorescent materials attached to, or associated with, the surface of the particle. These types of particles, in which fluorescent dyes or fluorescent particles are coupled directly to the surface of the particles in order to provide the classification fluorescence, are illustrated in U.S. Pat. No. 6,268,222 to Chandler et al. and U.S. Pat. No. 6,649,414 to Chandler et al., which are incorporated by reference as if fully set forth herein. The types of particles that can be used in the methods and systems described herein may also include particles having one or more fluorochromes incorporated into the core of the particles. Particles that can be used in the methods and systems described herein also include particles that in of themselves will exhibit one or more fluorescent signals upon exposure to one or more appropriate light sources. Furthermore, particles may be manufactured such that upon excitation the particles exhibit multiple fluorescent signals, each of which may be used separately or in combination to determine an identity of the particles.

Although the methods and systems are described herein with respect to "fluorescent light emitted by a particle," it is to be understood that this fluorescent light can include any fluorescent light emitted as a result of illumination of the particle by an excitation source. For example, as described above, the fluorescent light emitted by a particle can be light emitted by one or more fluorochromes attached to or incorporated into the particles or light emitted by the particles themselves. In this manner, the fluorescent light emitted by the particle may correspond to an identity of the particle. Alternatively, the fluorescent light emitted by the particle may correspond to a molecule that has reacted with an additional molecule attached to the particle. In other words, the fluorescent light emitted by the particle may be representative of one or more materials associated with the particle, which may include, for example, fluorescent biomolecules or other biomolecules attached to the surface of the particle (e.g., via one or more other biomolecules). In one particular example, an antigen may be coupled to the surface of the particle, which is then allowed to react with an antibody from a sample, which may also be allowed to react with a fluorescently labeled antibody. Therefore, the fluorescently labeled antibody is three molecules removed from the particle, but the fluorescently labeled antibody is associated with the particle through the reactions. Therefore, the methods and systems described herein may be used for measurement of fluorescence from surface bound, labeled biomolecules in one application. Additional examples of biomolecules that may be associated with the particle in a similar manner include, but are not limited to, nucleotides, polynucleotides, oligonucleotides, enzymes, etc.

To address the disadvantages of the currently available systems and methods for dynamic range expansion, which as discussed above in the description of the related art section include increasing the gain in later stages of the electrical system and adding noise to small signal levels, superior methods and systems are described herein that keep the high gain stages close to the front of the signal processing chain.

Turning now to the drawings, it is noted that the figures described herein are not drawn to scale. In particular, the scale of some of the elements of the figures are greatly exaggerated to emphasize characteristics of the elements. Some elements of the systems have not been included in the figures for the sake of clarity.

FIG. 1 illustrates one embodiment of a system configured to have an expanded or extended dynamic range (DR) that can be used for accurate measurement of the intensity of fluorescent light emitted from the brightest particles. The system may be configured as a flow cytometer. However, the system may be configured as any other measurement system that will benefit from having an expanded or extended DR. The system includes light source 10. Light source 10 is configured to illuminate particle 12 with light 14 as the particle flows through cuvette 16. Cuvette 16 may include any appropriate cuvette or other flow channel known in the art. Light source 10 may include any appropriate light source known in the art such as a laser, a laser diode, or a light emitting diode (LED). Preferably, the light source includes an excitation source. In other words, light source 10 is preferably configured to generate light 14 having one or more wavelengths such that upon illumination by the light, particle 12 will emit fluorescent light 18.

Fluorescent light 18 may be collected by lens 20. Lens 20 may include any appropriate lens known in the art. In addition, although lens 20 is shown in FIG. 1 to be a refractive optical component, it is to be understood that a reflective optical component may be used in place of lens 20 to collect the fluorescent light emitted by the particle. In addition, although lens 20 is shown in FIG. 1 to be a single lens, it is to be understood that lens 20 may be replaced with a multi-lens system. Furthermore, the system may optionally not include lens 20 or any other fluorescent light collector. Additionally, it is to be understood that the system shown in FIG. 1 may include more than one lens and/or other lenses. For example, the system may include a focusing lens (not shown) that is configured to focus light 14 onto particle 12.

The system also includes optical component 22, which is configured to split fluorescent light emitted by the particle into multiple light paths. In the embodiment shown in FIG. 1, optical component 22 is configured to split the fluorescent light collected by lens 20 into multiple light paths. The fluorescent light in the multiple paths has different intensities. The optical component may include, in one embodiment, a partially reflecting beam splitter or any other appropriate optical component known in the art. In one particular example, the optical component may include an uncoated beam splitter. An uncoated beam splitter will reflect about 4% of the incident energy (in this case, fluorescent light 18), and transmit the remaining portion of the incident energy (i.e., approximately 96% of the fluorescent light).

Note that while the intensity of the light transmitted by the optical component is lower than in standard flow cytometer configurations, assuming that the fluorescence saturation level on the particle has not been reached, this reduction in fluorescent light intensity can optionally and easily be compensated for by increasing the power (or intensity) of light source 10 in proportion to the intensity reduction.

As shown in FIG. 1, the optical component is configured to split the fluorescent light into two light paths. However, it is to be understood that the optical component may be configured to split the emitted fluorescent light into more than two light paths. For example, the optical component may include a wedge of glass having non-parallel surfaces, which may be configured as described further herein. In addition, optical component 22 may include any of the other optical components described herein which can be used to split a light beam into multiple light beams. Furthermore, it is to be understood that the system may include more than one optical component that is configured to split the fluorescent light into multiple light paths. For example, the system may include more than one partially reflecting beam splitter. The number of light paths into which the fluorescent light is split may vary depending on, for example, the number of different operating ranges of a detector and/or the different intensities that can be achieved in each of the multiple light paths.

The system also includes different channels configured to separately detect the fluorescent light in the multiple light paths. The different channels are also configured to generate multiple signals. Each of the multiple signals represents the fluorescent light in one of the multiple light paths. For example, as shown in FIG. 1, the system includes detectors 24 and 26, each of which constitutes at least a portion of one of the different channels. Detector 24 is configured to detect the fluorescent light transmitted by optical component 22. Detector 24 is also configured to generate a signal that represents the intensity of the fluorescent light in light path B (B for bright). Detector 24 may be a photomultiplier tube (PMT) or any other appropriate detector known in the art. For example, detector 24 may also be a photodiode, an avalanche photodiode, a charge coupled device (CCD), or a complementary metal-oxide-semiconductor (CMOS) detector. In addition, detector 24 may be any type of diode detector known in the art or any type of linear array type detector. Detector 26 is configured to detect the fluorescent light reflected by optical component 22. Detector 26 is also configured to generate a signal that represents the intensity of the fluorescent light in light path D (D for dim). Detector 26 may be a PMT or any other appropriate detector known in the art. For example, detector 26 may also be a photodiode, an avalanche photodiode, a CCD, or a CMOS detector. In addition, detector 26 may be any type of diode detector known in the art or any type of linear array type detector. Typically, detectors 24 and 26 will be the same type of detector, but will operate in different ranges (e.g., linear and non-linear) due to the different intensities of the fluorescent light in the different light paths.

As shown in FIG. 1, detectors 24 and 26 are coupled to electronic components 28 and 30, respectively. Electronic components 28 and 30 may include, for example, analog-to-digital (A/D) converters or any other suitable electronic components. In addition, electronic components 28 and 30 may form only a portion of the entire electronic chains of detectors 24 and 26, respectfully. For example, analog components (not shown) may be interposed between the detectors and the A/D converters. In addition, or alternatively, the electronics chains may include digital components (not shown) coupled to the output of the A/D converters. These optional analog and digital components may include any such suitable electronic components known in the art. In addition, the electronic chains coupled to detectors 24 and 26 may be similarly or differently configured.

The system shown in FIG. 1 also includes processor 32. Processor 32 is configured to determine which of the different channels is operating in a linear range based on the signals generated by the different channels. In addition, processor 32 is configured to alter the signal generated by the channel determined to be operating in the linear range to compensate for the different intensities. Processor 32 may include, for example, a digital signal processor (DSP) or any other suitable component that can be used to execute one or more program instructions to perform at least the functions described herein.

In one particular example based on the uncoated beam splitter optical component described above, the processor examines output integer values (B and D) from the A/D converters coupled to each of the detectors. Based on the signal levels, the processor determines which channel is operating in a linear range for the detectors. The processor also appropriately alters or scales the value corresponding to the channel operating in the linear range to compensate for the actual light level entering that photosensitive detector. For this simple example, the processor would multiply the D (dim) A/D output by 1/0.04=25 (if chosen), or alternately, the B (bright) A/D output by 1/0.96=1.041 (if chosen) to properly scale the result based on the division of light between the photosensitive detectors created by optical component 22. Such altering or scaling of the signal corresponding to the channel operating in the linear range effectively increases the dynamic range of the system by log 10(25/1.041)=1.38 decades. In this manner, altering of the signal by the processor increases the dynamic range of the system.

The processor may also be configured to perform a number of additional functions. For example, the processor may be configured to determine an intensity of the fluorescent light emitted by the particle from the altered signal. In addition, the processor may be configured to determine an identity of the particle from the intensity of the fluorescent light, possibly in combination with one or more other output signals generated by the system. Alternatively, the processor may be configured to determine an identity of a molecule attached to the surface of the particle or a reaction that has taken place on the surface of the particle from the intensity of the fluorescent light. In addition, the processor may be configured to determine a quantity of a molecule attached to the surface of the particle or a reaction that has taken place on the surface of the particle from the intensity of the fluorescent light. The processor may also be configured to perform any other function typically performed in flow cytometer data analysis.

The dynamic range improvement described above could be further increased by increasing the difference between the intensities of the fluorescent light in the multiple light paths. In one such embodiment, the intensity of the light reflected by optical component 22 may be reduced by applying an anti-reflective coating (not shown) to the input face of the optical component. In another embodiment, as shown in FIG. 1, the system may include additional optical component 34 positioned in the light path of the lower intensity fluorescent light between optical component 22 and detector 26. The additional optical component is configured to decrease the intensity of the fluorescent light in this light path. Additional optical component 34 may include any optical component that can be used to reduce the intensity of the fluorescent light such as a neutral density filter. Each of these configurations effectively reduces the intensity of the fluorescent light detected by detector 26, thus further expanding or extending the DR of the system.

The system shown in FIG. 1 may be further configured as described herein. In addition, although the system shown in FIG. 1 is configured to have an expanded or extended DR for only one fluorescent measurement, it is to be understood that if multiple fluorescent measurements are performed by the system, the DR of the system may be expanded for each, or more than one, of the fluorescent measurements in a manner as described above. For example, the fluorescent light emitted by the particle may be separated by wavelength using, in one example, one or more dichroic beam splitters (not shown). In this manner, the fluorescent light may be separated based on the fluorochrome that emitted the fluorescent light. As such, fluorescent light corresponding to an identity of the particle may be separated from fluorescent light corresponding to a molecule attached to the particle (e.g., via a reaction with another molecule attached to the surface of the particle). In addition, two or more of the fluorescent light paths generated by the one or more dichroic beam splitters may be split into multiple light paths as described above such that the fluorescent light in the multiple light paths has different intensities. The fluorescent light in the multiple light paths may then be detected and processed as described above.

One method for expanding a dynamic range of a system, which can be performed by the system shown in FIG. 1, includes splitting fluorescent light into multiple light paths. The fluorescent light in the multiple light paths has different intensities. The method also includes detecting the fluorescent light in the multiple light paths with different channels to generate multiple signals. Each of the multiple signals represents the fluorescent light in one of the multiple light paths. In addition, the method includes determining which of the different channels is operating in a linear range based on the multiple signals. The method further includes altering the signal generated by the channel determined to be operating in the linear range to compensate for the different intensities.

In one embodiment, the system may be configured as a flow cytometer or another measurement system that will benefit from having an extended or expanded DR. In another embodiment, the method may include determining an intensity of the fluorescent light emitted by the particle from the altered signal. Altering the signal as described above increases the dynamic range for the system.

In some embodiments, the fluorescent light in a first of the multiple light paths is lower in intensity than the fluorescent light in a second of the multiple light paths. In one such embodiment, the method includes prior to the detecting step, decreasing the intensity of the fluorescent light in the first of the multiple light paths. Each of the embodiments of the method described above may include any other step(s) described herein.

While the system and method embodiments described above advantageously keep the high gain at the beginning of the processing chain for small signals, the system and method described above is more expensive due to the added expense of the second photosensitive detector, analog electronics, and A/D conversion circuitry. Fortunately, because of the geometry of a flow cytometer, there is another way to accomplish this multiple light level measurement with far fewer components.

For example, another method and system involves using multiple illumination zones spatially separated along the flow path of a particle. In a flow cytometer as described above, a particle being measured travels along a generally straight path through a cuvette, passing through an illumination zone which results in excitation of one or more fluorochromes associated with the particle. The resulting fluorescent light is projected, focused, and/or imaged on a portion of a detector's photosensitive area, while the particle is illuminated in the illumination zone, and a single current pulse is generated by the detector as a result. The collector or pickup lens magnification may be selected such that the florescent light emitted by the particle fills only a portion of the photosensitive area of the detector. In other words, the photosensitive area of the detector may be relatively long in comparison to the cross-sectional area of the fluorescent light beam projected, focused, and/or imaged onto the detector. Therefore, theoretically, the particle can still be "seen" by the detector when the particle is not located within the illumination zone. However, no signal will be produced by the detector when the particle is not located in the illumination zone since the fluorescence will extinguish quickly without excitation of the fluorochrome(s) associated with the particle. Thus, the width of the pulse generated by the detector is generally proportional to the length of time that the particle is located in the illumination zone.

It is possible, therefore, to take advantage of the spatially "long" photosensitive area of the detector for the dynamic range extension methods and systems described herein. For example, a second, but less bright illumination zone, can be added to the system, which is spatially separated from the primary illumination zone. As such, fluorescent light emitted by a particle as a result of illumination in both of these illumination zones can be directed to different portions of the photosensitive area of the detector. In this manner, the detector will generate two time-separated current pulses, and one pulse would be much larger than the other due to the different intensities of the light in the illumination zones.

A processor such as a DSP can be configured to measure the amplitude of each current pulse and, similar to the methods described above, determine which signal is located in a linear range of the detector. The processor may also be configured to alter or scale the signal located in the linear range in proportion to the ratio of the illumination zone excitation energies. Thus, only a single detector and associated electronics may be included in the system. As such, the systems described below avoid the costs associated with multiple detectors and corresponding electronics. However, the challenge now becomes to provide a cost effective way to create the additional, dimmer illumination zone(s). To address this challenge, several embodiments of a system have been identified and are described further herein, which provide cost effective ways to illuminate a particle in multiple illumination zones with light having different intensities.

It is important to note that the order of the bright and dim illumination zones may be important. In particular, preferably, the particle travels through the dim illumination zone first, then through the bright illumination zone. In contrast, if the particle travels through the bright illumination zone before the dim illumination zone, the analog electronics may not settle in time to accurately reproduce the pulse resulting from illumination of the particle in the dim illumination zone. Another factor in selecting the order in which the particle travels through the illumination zones is the potential for photo-degradation of the fluorochrome(s) associated with the particle due to illumination in the bright illumination zone. Therefore, it may be preferable to illuminate the particle in the dim illumination zone first, then in brighter illumination zones.

Figure 2:
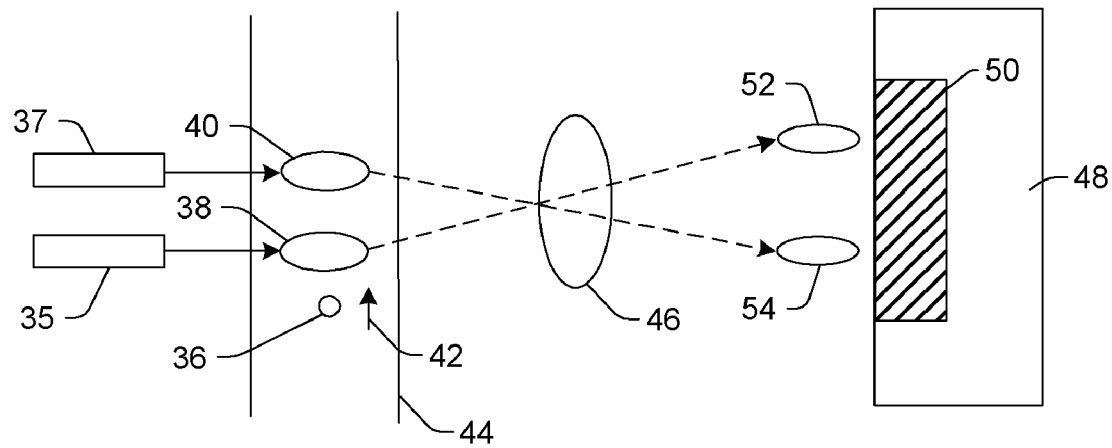
FIG. 2 is a schematic diagram illustrating a cross-sectional view of an embodiment of a system configured to have an expanded DR that includes an illumination subsystem configured to illuminate a particle in multiple illumination zones with light having different intensities.

FIG. 2 illustrates one embodiment of a system configured to have an expanded DR. The system includes an illumination subsystem, which includes light sources 35 and 37. Light sources 35 and 37 are configured to illuminate particle 36 in multiple illumination zones 38 and 40, respectively, with light that has different intensities. Although the illumination subsystem is shown in FIG. 2 to include two light sources, it is to be understood that the system shown in FIG. 2 may include two or more light sources. In an alternative, the illumination subsystem may include a single light source coupled to a beam multiplier, which may include any of the beam multipliers as described herein.

As shown in FIG. 2, illumination zones 38 and 40 are spaced apart along flow path 42 of particle 36. In this manner, as particle 36 moves through cuvette 44, which may be configured as described above, the particle is located in illumination zone 38, then in illumination zone 40. In this manner, for the reasons described above, the illumination subsystem is preferably configured such that the light directed to the particle in illumination zone 38 has a lower intensity than the light directed to the particle in illumination zone 40. The illumination subsystem may be further configured as described herein. In addition, although two illumination zones are shown in FIG. 2, it is to be understood that the illumination subsystem may be configured to illuminate the particle in more than two illumination zones, each of which is spatially separated along the flow path of the particle.

As further shown in FIG. 2, fluorescent light emitted by the particle in the different illumination zones may be collected by lens 46. Lens 46 may be configured as described above. In addition, it is to be understood that lens 46 may optionally not be included in the system.

The system shown in FIG. 2 also includes a detection subsystem that is configured to separately detect fluorescent light emitted by the particle while the particle is located in the multiple illumination zones. The detection subsystem is also configured to generate multiple signals, each of which represents the fluorescent light emitted by the particle while the particle is located in one of the multiple illumination zones. For example, in this embodiment, the detection subsystem includes detector 48 having photosensitive area 50. In this manner, the detection subsystem includes a single detector. Detector 48 may be a PMT or any other suitable detector known in the art such as a photodiode, an avalanche photodiode, a CCD, a CMOS detector, or any other suitable type of diode or linear array detector known in the art.

As shown in FIG. 2, photosensitive area 50 is larger than an area of fluorescent light 52 emitted by the particle while the particle is located in illumination zone 38. Photosensitive area 50 is also larger than an area of fluorescent light 54 emitted by the particle while the particle is located in illumination zone 40. Furthermore, photosensitive area 50 is larger than a combined area of fluorescent light 52 and 54. In this manner, fluorescent light 52 and 54 may be directed to spatially separated portions of photosensitive area 50. In an alternative embodiment, the detection subsystem may include multiple detectors (not shown) in place of detector 48. Fluorescent light emitted by the particle due to illumination in each of the illumination zones may be directed to a different detector. In some such embodiments, each of the multiple detectors may be a PMT or any other suitable detector known in the art such as a photodiode, an avalanche photodiode, a CCD, a CMOS detector, or any other suitable type of diode or linear array detector known in the art.

Figure 3:
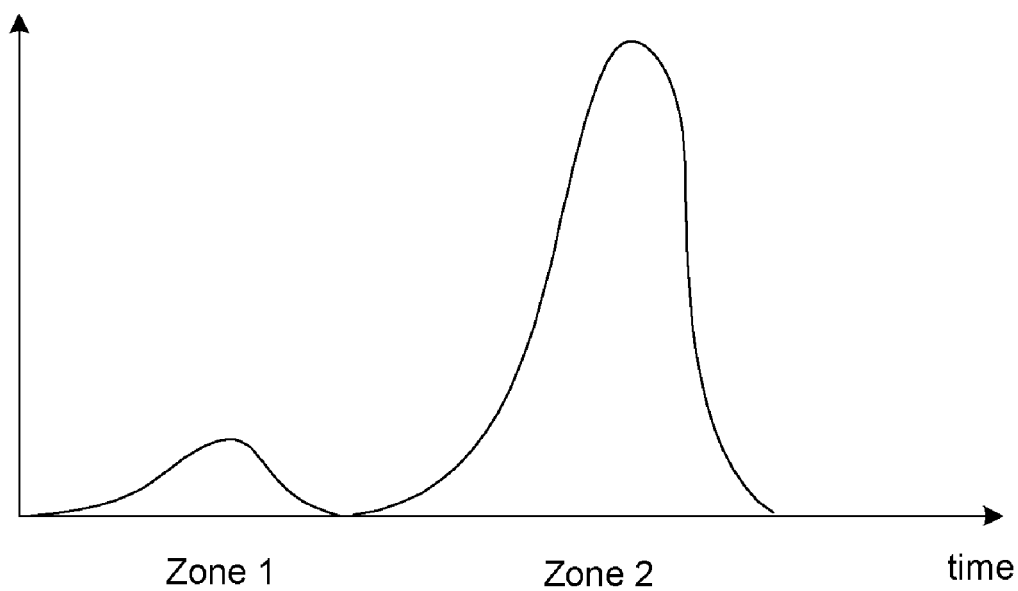
FIG. 3 is a graph illustrating examples of multiple signals that may be generated by separately detecting fluorescent light emitted by a particle while the particle is located in multiple illumination zones.

When particle 36 is located in illumination zone 38, detector 48 will generate a signal that represents fluorescent light 52. When particle is located in illumination zone 40, detector 48 will generate a signal that represents fluorescent light 54. FIG. 3 is a plot showing examples of signals that can be generated by the detection subsystem of FIG. 2 and other embodiments described herein. As shown in FIG. 3, the signal generated by the detection subsystem representing light emitted by the particle while the particle is located in the first illumination zone (e.g., illumination zone 38) has a much lower value than the signal generated by the detection system representing fluorescent light emitted by the particle while the particle is located in the second illumination zone (e.g., illumination zone 40). The difference in the values of the signals is a direct result of the intensity of the light illuminating the particle in the different illumination zones. Preferably, the intensities of the light illuminating the particle in the different illumination zones is selected such that one of the signals will be generated in the linear operating range of the detector.

The system also includes a processor (not shown), which may be coupled to the detector as described above (e.g., via one or more analog and/or digital electronic components). The processor is configured to determine which of the multiple signals generated by detector 48 due to illumination of the particle in one of the multiple illumination zones is produced in a linear range of the detector. The processor is also configured to alter or scale the signal located in the linear range of the detector to compensate for the different intensities. For example, the processor may be configured to scale the signal located in the linear range of the detector in proportion to the different intensities of the light illuminating the particle in the different illumination zones. The processor may be further configured as described above. In addition, the system shown in FIG. 2 may be further configured as described herein.

The illumination subsystem described in FIG. 2 may include two or more light sources such as lasers. Each of the light sources may be configured to provide illumination for one of the multiple illumination zones. Adding one or more additional light sources such as lasers to the system increases the cost of the system. Since the intensity of the light in one illumination zone is preferably much less than that of the other, an inexpensive LED and relatively narrow band pass filter could be employed as the secondary light source. In this manner, an additional light source may be added to the system without substantially increasing the cost of the system. However, in other embodiments described herein, the system may include a single light source coupled to one or more optical components that are configured to split the light generated by the single light source into multiple light beams having different intensities.

Figure 4:
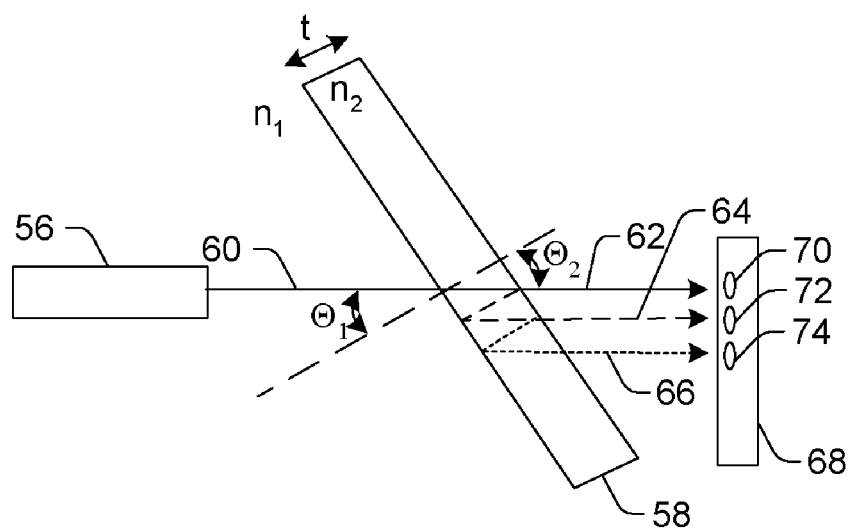
FIGS. 4-8 are schematic diagrams illustrating cross-sectional views of different embodiments of an illumination subsystem configured to illuminate a particle in multiple illumination zones with light having different intensities that may be included in a system configured to have an expanded DR.

FIG. 4 illustrates one embodiment of an illumination subsystem that may be included in a system configured to have an expanded DR. As shown in FIG. 4, the illumination subsystem includes single light source 56 such as a laser, which is coupled to glass slide 58 arranged in a path of light beam 60 emitted by single light source 56. In addition, as shown in FIG. 4, glass slide 58 is arranged at an angle, $\Theta_1$, with respect to light beam 60. In this manner, the glass slide may be configured as a beam multiplier. For example, light beam 60 enters glass slide 58 and at the boundary of the uncoated air to glass interface of glass slide 58, a portion of light beam 60 is reflected back towards the light source. Therefore, light beam 62 exiting glass slide 58 has an intensity that is lower than an intensity of the light beam generated by the single light source. A portion of this reflected light once again partially reflects off of the first surface of glass slide 58, and then exits the second surface as light beam 64. Since a relatively small portion of light beam 60 is reflected back toward the light source, and a portion of the light beam reflected off of the first surface of glass slide 58 will again be reflected by the second surface of the glass slide, light beam 64 will have a lower intensity than light beam 62. Additional light beams such as light beam 66 may be generated in this manner. Each of the additional light beams will have a lower intensity than the light beams that previously exited the glass slide.

Since the glass slide is canted at an angle with respect to the single light source, there is a physical separation between light beams 62, 64, and 66. As such, light beams 62, 64, and 66 may be directed to illumination zones 70, 72, and 74, respectively, which are spaced apart along a flow path of the particle (not shown). As the particle travels through cuvette 68, the particle will travel through illumination zone 74. After traveling through illumination zone 74, the particle will travel through illumination zone 72, which has an intensity that is greater than that of illumination zone 74. After traveling through illumination zone 72, the particle will travel through illumination zone 70, which has an intensity that is greater than that of illumination zone 72. In this manner, as described above, the particle will be illuminated in the illumination zones having progressively higher intensities. The distance between the light beams is generally proportional to this angle $\Theta_1$.

The angle of the glass slide can be selected such that light beams 62, 64, and 66 are substantially parallel to one another and have substantially the same diameters. As such, a single focusing lens (not shown) may be configured to focus the light beams exiting the glass slide onto the path along which the particle travels in the cuvette. Alternatively, or in addition, a focusing lens (not shown) may be positioned in the path of the light beam generated by single light source 56. In addition, a single collection lens (not shown) may be configured to collect the fluorescent light emitted by the particle. The focusing and collecting lenses may be further configured as described above.

Furthermore, the intensity of each relatively low intensity beam that exits the glass slide will be reduced significantly. For example, in the case where the reflection coefficient at the air-glass interface is 2%, the reduction can be calculated by comparing the relative intensities of beams 62 and 64 as log 10(0.02×0.02×0.98)=3.4 decades. Therefore, the first two beams of the illumination subsystem shown in FIG. 4 can add more than three decades of DR between the illumination zones. Note that an additional 3.4 decade reduced beam (e.g., light beam 66) (−6.8 decades from the primary) will be present, and could potentially be used as a third illumination zone. This pattern of reduced intensity light beams repeats with decreasing magnitude, but it is expected that the dynamic range of the particle and chemistry, or instrument electronics, may limit the useful light beams to two or three. The separation distance between each parallel ray is preferably, at a minimum, equivalent to the diameter of the laser beam. Since the beam diameter is typically focused to a spot having a diameter of tens of microns at cuvette 68, the necessary thickness t of the glass slide will decrease as the glass slide is placed closer to the cuvette.

A system that includes the illumination subsystem shown in FIG. 4 may be further configured as described herein. For example, such a system also includes a detection subsystem that is configured to separately detect fluorescent light emitted by the particle while the particle is located in the multiple illumination zones. The detection subsystem is also configured to generate multiple signals, each of which represents the fluorescent light emitted by the particle while the particle is located in one of the multiple illumination zones. The detection subsystem may be further configured as described herein. In addition, such a system includes a processor that is configured to determine which of the multiple signals is located in a linear range and to alter the signal located in the linear range to compensate for the different intensities. The processor may be further configured as described herein.

Figure 5:
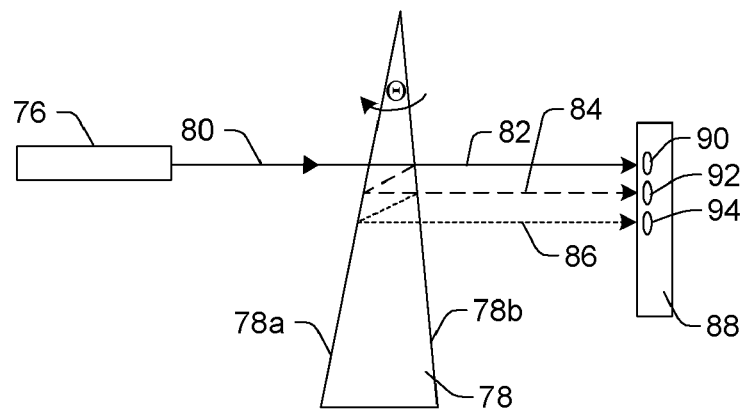

FIG. 5 illustrates another embodiment of an illumination subsystem that may be included in a system configured to have an expanded DR. As shown in FIG. 5, the illumination subsystem includes single light source 76. Single light source 76 may include a laser or any other appropriate light source known in the art. The illumination subsystem also includes wedge of glass 78. Wedge of glass 78 has non-parallel surfaces (e.g., surfaces 78a and 78b) arranged in a path of light beam 80 emitted by single light source 76. Light beam 80 enters the wedge of glass, and like the glass slide described above, a portion of the light beam will be reflected back towards the single light source. The portion of the light transmitted through the wedge of glass forms light beam 82. Since a relatively large portion of light beam 80 will be transmitted by wedge of glass 78, light beam 82 will be the brightest light beam exiting wedge of glass 78. In other words, of the light beams that exit the wedge of glass, light beam 82 will have the highest intensity.

The portion of light beam 80 reflected back toward the single light source will again be reflected (at least partially) by the entrance face (e.g., surface 78a) of the wedge of glass. A portion of this light beam will exit the wedge of glass as light beam 84. Light beam 84 obviously will have a lower intensity than light beam 82. A portion of the original light beam will be reflected again within the wedge of glass and may exit the wedge of glass as light beam 86. Light beam 86 will have the lowest intensity of light beams 82, 84, and 86. Obviously, additional light beams may also exit the wedge of glass, and if the additional light beams have sufficient intensity, these light beams may also used for illumination of a particle.

Light beams 82, 84, and 86 are directed to cuvette 88 through which a particle (not shown) will move during measurements. In particular, light beams 82, 84, and 86 are directed to the cuvette in multiple illumination zones 90, 92, and 94, respectively, arranged one after another along a flow path of the particle. The particle will preferably move through the illumination zone having the lowest intensity (e.g., illumination zone 94) first and the highest intensity (e.g., illumination zone 90) last for the reasons set forth above. Due to the non-parallel surfaces of the wedge of glass, light beams 82, 84, and 86 will be directed to spaced apart locations along the flow path of the particle. In addition, the distance between beams 82, 84, and 86 will be larger than that between the beams produced by the glass slide shown in FIG. 4 for the same (average glass thickness). The distance between beams 82, 84, and 86 can also be altered by changing the angle, Θ, between the entrance face and exit face of the wedge of glass.

The illumination subsystem may also include a focusing lens (not shown). In one example, the focusing lens may be placed in a path of light beam 80 between single light source 76 and wedge of glass 78. However, if a wedge of glass with non-parallel surfaces is used as the beam multiplier, the distance between beams 82, 84, and 86 is larger than that between the beams produced by the glass slide shown in FIG. 4 for the same (average) glass thickness, making it more feasible to place the beam multiplier between the laser and focusing lens, where the beam width is widest. In this manner, the focusing lens may be positioned in the optical paths of light beams 82, 84, and 86 between the wedge of glass and cuvette 88. The focusing lens may be further configured as described above. A system that includes an illumination subsystem as shown in FIG. 5 may be further configured as described herein.

Figure 6:
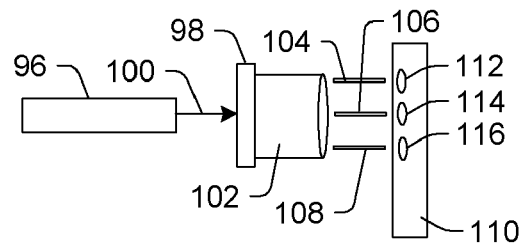

FIG. 6 illustrates another embodiment of an illumination subsystem that may be included in a system configured to have an expanded DR. As shown in FIG. 6, the illumination subsystem includes single light source 96. Single light source 96 may include a laser or any other appropriate light source known in the art. This illumination subsystem also includes beam expander 98. Beam expander 98 is configured to increase a cross-sectional area of light beam 100. Light beam 102 exiting the beam expander is directed to the input faces of multiple fiber optic cables 104, 106, and 108. Fiber optic cables 104, 106, and 108 may include any appropriate fiber optic cables known in the art. As shown in FIG. 6, fiber optic cables 104, 106, and 108 are arranged such that each of the fiber optic cables directs light to cuvette 110 in a different illumination zone. In particular, fiber optic cables 104, 106, and 108 direct light to multiple illumination zones 112, 114, and 116, respectively, which are spaced apart along a flow path of a particle (not shown). In addition, although the illumination subsystem is shown in FIG. 6 to include three fiber optic cables, it is to be understood that the illumination subsystem may include two or more fiber optic cables arranged in such an optical configuration.

Since beam expander 98 will produce an expanded light beam that has a relatively constant intensity across the cross-sectional area of the light beam, each of the fiber optic cables may receive a substantially equal amount of light. In this manner, the illumination subsystem may also include one or more optical components (not shown) such as neutral density filters either at an input face or an output face of one or more of the fiber optic cables. The one or more optical components may be configured to alter the intensity of the light exiting one or more of the fiber optic cables such that the particle is illuminated in the multiple illumination zones with light having different intensities. Preferably, the particle is illuminated as it travels along the flow path with light having relatively low intensity then light having higher intensity for the reasons set forth above.

In other embodiments, optical components other than a beam expander may be used to direct light from a single light source to multiple fiber optic cables substantially simultaneously. For example, an uncoated beam splitter such as that shown in FIG. 1 may be used to split the light from the single light source into multiple light beams having different intensities. Each of the multiple light beams may then be directed to one of the multiple fiber optic cables. Obviously, many other optical configurations may be used to deliver light from a single light source to multiple fiber optic cables, and the description provided herein is not intended to limit the optical configurations that can be used in this system embodiment.

The illumination subsystem shown in FIG. 6 may also include a focusing lens (not shown). In one example, the focusing lens may be placed in a path of light beam 100 between single light source 96 and beam expander 98. Alternatively, the focusing lens may be positioned in the optical path of light beam 120 between the beam expander and fiber optic cables 104, 106, and 108. In yet another alternative, the focusing lens may be positioned in the optical path of light exiting fiber optic cables 104, 106, and 108 between the fiber optic cables and cuvette 110. The focusing lens may be further configured as described above. A system that includes the illumination subsystem shown in FIG. 6 may be further configured as described herein.

Figure 7:
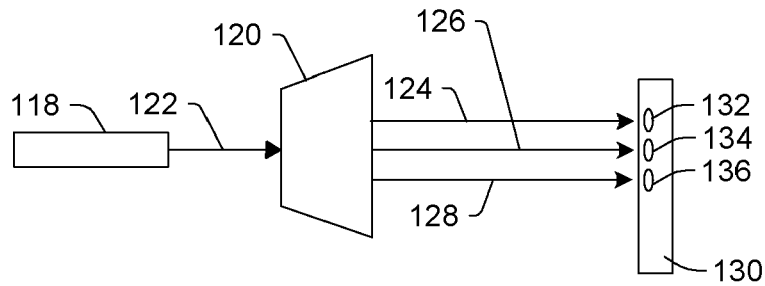

FIG. 7 illustrates another embodiment of an illumination subsystem that may be included in a system configured to have an expanded DR. As shown in FIG. 7, the illumination subsystem includes single light source 118. Single light source 118 may include a laser or any other appropriate light source known in the art. The illumination subsystem also includes demultiplexer 120. Demultiplexer 120 is configured to receive light beam 122 generated by light source 118 and to separate light beam 122 into individual light beams (e.g., light beams 124, 126, and 128). The demultiplexer is preferably configured to separate light beam 122 into individual light beams having different intensities. However, if the demultiplexer is not configured to generate individual light beams having different intensities, the illumination subsystem may include one or more components (not shown) positioned in a path of one or more of the individual light beams such as a neutral density filter or any other components that can alter the intensity of the individual light beams. Demultiplexer 120 may include any appropriate demultiplexer known in the art. In addition, although demultiplexer 120 is shown in FIG. 7 to generate three individual light beams, it is to be understood that the demultiplexer may be configured to generate two or more individual light beams.

Individual light beams 124, 126, and 128 are directed from the demultiplexer to cuvette 130 through which a particle (not shown) will move during measurement. In particular, individual light beams 124, 126, and 128 are directed to multiple illumination zones 132, 134, and 136, respectively, which are spaced apart along a flow path through cuvette 130. Preferably, the intensity of the light in illumination zone 136 is lower than that in illumination zones 134 and 132, and the intensity of the light in illumination zone 134 is lower than that in illumination zone 132. In this manner, as the particle travels along the flow path, it will be illuminated first with low intensity light then increasingly higher intensity light as it moves through the different illumination zones. As further shown in FIG. 7, the individual light beams exiting the demultiplexer may be spaced apart such that the spacing between the individual light beams exiting the demultiplexer defines the spacing between the multiple illumination zones. However, the spacing between the multiple illumination zones may be altered using one or more optical components (not shown) positioned in the path of the individual light beams and configured to alter a direction of the individual light beams (e.g., by refraction).

The illumination subsystem may also include one or more demultiplexers, which may be configured as described above, coupled to the single light source. The illumination subsystem shown in FIG. 7 may further include a focusing lens (not shown). In one example, the focusing lens may be placed in a path of light beam 122 between single light source 118 and demultiplexer 120. Alternatively, the focusing lens may be positioned in the optical paths of light beams 124, 126, and 128 between the demultiplexer and cuvette 130. The focusing lens may be further configured as described above. A system that includes an illumination subsystem as shown in FIG. 7 may be further configured as described herein.

Figure 8:
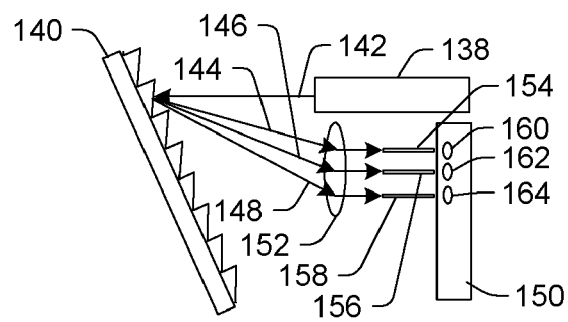

FIG. 8 illustrates another embodiment of an illumination subsystem that may be included in a system configured to have an expanded DR. As shown in FIG. 8, the illumination subsystem includes single light source 138. Single light source 138 may include a laser or any other appropriate light source known in the art. The illumination subsystem also includes diffraction grating 140 arranged in a path of light beam 142 emitted by light source 138. Diffraction grating 140 is configured to reflect light beam 142 generated by light source 138 into multiple light beams 144, 146, and 148.

Each of the multiple light beams may include one of the different orders of light that is reflected from the diffraction grating. In particular, when a monochromatic source such as a laser is directed to a lined diffraction grating, multiple beams are reflected at different orders, and the intensity of each light beam is reduced as the "order" increases (e.g., the zero order reflected beam will be brighter than the first order reflected beam, and so on). In this manner, light beam 144 may include the zero order light reflected from diffraction grating 140. Therefore, light beam 144 will have the highest intensity of the light beams reflected from the diffraction grating. Light beam 146 may include the first order light reflected from the diffraction grating. In this manner, light beam 146 will have an intensity that is lower than light beam 144. Likewise, light beam 148 may include the second order light reflected from diffraction grating 140 and, therefore, will have the lowest intensity of the three light beams. The diffraction grating is also configured to reflect the different orders of light in different directions. Therefore, the diffraction grating may generate individual light beams that have both different intensities and adequate spacing for the multiple illumination zone configuration. In addition, the line spacing of the diffraction grating could be varied to change the angle of each order, and the intensity of the light beam reflected at each order. Furthermore, more than three orders of light may be reflected from the diffraction grating, and the number of orders which are directed to cuvette 150 may vary depending on how many of the different orders have sufficient intensity for particle measurements.

As shown in FIG. 8, the illumination subsystem may also include focusing lens 152. Focusing lens 152 may be configured to receive light reflected from the diffraction grating and to direct the different orders of light to different fiber optic cables. In particular, light beams 144, 146, and 148 may be directed to fiber optic cables 154, 156, and 158, respectively. Fiber optic cables 154, 156, and 158 may be configured to direct the different orders of light to multiple illumination zones 160, 162, and 164, respectively, which are spaced apart along the flow path of the particle (not shown) within cuvette 150. Light in illumination zone 164 has a lower intensity than the light in illumination zones 162 and 160, and light in illumination zone 162 is lower in intensity than the light in illumination zone 160. In this manner, as the particle travels through the illumination zones, it is illuminated with lower intensity light first, and then with increasingly higher intensities of light. Focusing lens 152 may be further configured as described above. In addition, focusing lens may be located in a different position within the illumination subsystem (e.g., between light source 138 and diffraction grating 140). Fiber optic cables 154, 156, and 158 may include any appropriate fiber optic cables known in the art. In addition, the illumination subsystem shown in FIG. 8 may not include the fiber optic cables. In one such alternative, light from lens 152 may be directly focused to cuvette 150. A system that includes the illumination subsystem shown in FIG. 8 may be further configured as described herein.

One method for expanding a dynamic range of a system, which can be performed by the system shown in FIG. 2 and a system, which includes an illumination subsystem as shown in FIGS. 4-8, includes illuminating a particle in multiple illumination zones with light having different intensities. The method also includes separately detecting fluorescent light emitted by the particle while the particle is located in the multiple illumination zones to generate multiple signals. Each of the multiple signals is representative of the fluorescent light emitted by the particle in one of the multiple illumination zones. In addition, the method includes determining which of the multiple signals is located in a linear range. The method further includes altering the signal located in the linear range to compensate for the different intensities.

In one embodiment, the multiple illumination zones are spaced apart along a flow path of the particle, and a first of the multiple illumination zones in which the particle is first located is lower in intensity than a second of the multiple illumination zones in which the particle is subsequently located. The fluorescent light emitted by the particle may correspond to an identity of the particle. Alternatively, the fluorescent light emitted by the particle corresponds to a molecule reacted with an additional molecule attached to the particle. Each of the embodiments of the method described above may include any other step(s) described herein.

Although the above methods and systems are described with respect to flow cytometry applications, it is to be understood that the methods and systems described herein may be used in other applications. For example, the methods and systems described herein may be used for absorption spectroscopy applications. In absorption techniques, such as infrared (IR) and ultraviolet-visible (UV-Vis), light is focused on a sample, and a detector measures the light not absorbed by the sample, which is known as the transmitted light. Obviously, in highly absorbing or concentrated samples, the transmittance is low, and in dilute, or low absorbing samples transmittance is high. Therefore, in some instances, increasing the dynamic range as described herein in absorption spectroscopy applications may be advantageous.

It will be appreciated to those skilled in the art having the benefit of this disclosure that this invention is believed to provide methods and systems for dynamic range expansion. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for expanding a dynamic range of a system, comprising:

splitting fluorescent light emitted by a particle into multiple light paths, wherein the fluorescent light in the multiple light paths has different intensities;

detecting the fluorescent light in the multiple light paths with different channels to generate multiple signals, wherein each of the multiple signals represents the fluorescent light in one of the multiple light paths;

determining which of the different channels is operating in a linear range based on the multiple signals; and altering the signal generated by the channel determined to be operating in the linear range to compensate for the different intensities.

2. The method of claim 1, wherein the fluorescent light emitted by the particle corresponds to an identity of the particle.

3. The method of claim 1, wherein the fluorescent light emitted by the particle corresponds to a molecule reacted with an additional molecule attached to the particle.

4. The method of claim 1, wherein the system is configured as a flow cytometer.

5. The method of claim 1, further comprising determining an intensity of the fluorescent light emitted by the particle from the altered signal.

6. The method of claim 1, wherein said altering increases the dynamic range for the system.

7. The method of claim 1, wherein the fluorescent light in a first of the multiple light paths is lower in intensity than the fluorescent light in a second of the multiple light paths, the method further comprising prior to said detecting, decreasing the intensity of the fluorescent light in the first of the multiple light paths.

8. A system configured to have an expanded dynamic range, comprising:

an optical component configured to split fluorescent light emitted by a particle into multiple light paths, wherein the fluorescent light in the multiple light paths has different intensities;

different channels configured to separately detect the fluorescent light in the multiple light paths and to generate multiple signals, wherein each of the multiple signals represents the fluorescent light in one of the multiple light paths; and a processor configured to determine which of the different channels is operating in a linear range based on the multiple signals and to alter the signal generated by the channel determined to be operating in the linear range to compensate for the different intensities.

9. The system of claim 8, wherein the fluorescent light emitted by the particle corresponds to an identity of the particle.

10. The system of claim 8, wherein the fluorescent light emitted by the particle corresponds to a molecule reacted with an additional molecule attached to the particle.

11. The system of claim 8, wherein the system is further configured as a flow cytometer.

12. The system of claim 8, wherein the processor is further configured to determine an intensity of the fluorescent light emitted by the particle from the altered signal.

13. The system of claim 8, wherein altering of the signal by the processor increases the dynamic range of the system.

14. The system of claim 8, wherein the fluorescent light in a first of the multiple light paths is lower in intensity than the fluorescent light in a second of the multiple light paths, wherein the system further comprises an additional optical component positioned in the first of the multiple light paths between the optical component and one of the different channels, and wherein the additional optical component is configured to decrease the intensity of the fluorescent light in the first of the multiple light paths.

* * * * *